United States Patent
Kahn et al.

(10) Patent No.: US 7,343,260 B1
(45) Date of Patent: Mar. 11, 2008

(54) METHOD AND APPARATUS TO PROVIDE AN INTERFACE TO OBTAIN DATA FROM A REAL-TIME MONITOR

(75) Inventors: Philippe Kahn, Aptos, CA (US); Arthur Kinsolving, Santa Cruz, CA (US)

(73) Assignee: FullPower, Inc., Santa Cruz, CA (US)

( * ) Notice: Subject to any disclaimer, the term of this patent is extended or adjusted under 35 U.S.C. 154(b) by 62 days.

(21) Appl. No.: 11/173,753

(22) Filed: Jun. 30, 2005

(51) Int. Cl.
*G06F 19/00* (2006.01)

(52) U.S. Cl. ...................................... 702/122; 709/201
(58) Field of Classification Search ................ 702/122, 702/182–185, 188, 118; 714/25; 709/100, 709/201
See application file for complete search history.

(56) References Cited

U.S. PATENT DOCUMENTS

| | | |
|---|---|---|
| 5,960,085 A | 9/1999 | de la Huerga |
| 6,408,330 B1 | 6/2002 | DeLaHuerga |
| 6,788,980 B1* | 9/2004 | Johnson .................... 700/1 |
| 2003/0208113 A1 | 11/2003 | Mault et al. |
| 2003/0236625 A1 | 12/2003 | Brown et al. |
| 2004/0017300 A1 | 1/2004 | Kotzin et al. |
| 2004/0024846 A1 | 2/2004 | Randall et al. |
| 2004/0043760 A1 | 3/2004 | Rosenfeld et al. |
| 2004/0044493 A1 | 3/2004 | Coulthard |
| 2004/0078219 A1 | 4/2004 | Kaylor et al. |
| 2004/0078220 A1 | 4/2004 | Jackson |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0146048 A1 | 7/2004 | Cotte |
| 2004/0148340 A1 | 7/2004 | Cotte |
| 2004/0148341 A1 | 7/2004 | Cotte |
| 2004/0148342 A1 | 7/2004 | Cotte |
| 2004/0148351 A1 | 7/2004 | Cotte |
| 2004/0148392 A1 | 7/2004 | Cotte |
| 2005/0027567 A1* | 2/2005 | Taha ............................ 705/2 |
| 2005/0101841 A9 | 5/2005 | Kaylor et al. |
| 2005/0107944 A1 | 5/2005 | Hovestadt et al. |
| 2005/0113650 A1 | 5/2005 | Pacione et al. |
| 2005/0182824 A1 | 8/2005 | Cotte |

(Continued)

OTHER PUBLICATIONS

YAHOO, Inc. http://help.yahoo.com/help/us/alerts/index.html.

(Continued)

*Primary Examiner*—Edward Raymond
(74) *Attorney, Agent, or Firm*—Blakely, Sokoloff, Taylor & Zafman, LLP; Judith A. Szepesi (57) ABSTRACT

A method and apparatus for a plug-in apparatus to provide server-transmission from a sensor, monitor, or device (SMD), the plug-in apparatus comprising an interface to automatically receive data from the SMD, without interfering or affecting SMD functionality, and a transmitter to wirelessly transmit the data from the SMD to a remote server, the data from the SMD representing monitoring results.

8 Claims, 8 Drawing Sheets

U.S. PATENT DOCUMENTS

2006/0249683 A1*  11/2006  Goldberg et al. ...... 250/370.01
2007/0017136 A1*  1/2007  Mosher et al. ................ 40/633

OTHER PUBLICATIONS

YAHOO, Inc. http://help.yahoo.com/help/us/alerts/alerts-18.html.
YAHOO, Inc. http://help.yahoo.com/help/us/alerts/-08.html.
YAHOO, Inc. http://help.yahoo.com/help/us/alerts/alerts-05.html.
YAHOO, Inc. http://help.yahoo.com/help/us/alerts/alerts-21.html.
YAHOO, Inc. http://help.yahoo.com/help/us/alerts/alerts-16.html.
YAHOO, Inc. http://alerts.yahoo.com/main.php?view=splash_sighnup_signin&.done=http%3A%2F%2Fal....
YAHOO, Inc. http://help.yahoo.com/help/us/mobile/.
YAHOO, Inc. http://help.yahoo.com/help/us/auct.
YAHOO, Inc., http://login.yahoo.com/config/login?.slogin=&.intl=us&src=&.bypass.partner=&.done....
YAHOO, Inc. http://help.yahoo.com/help/us/alerts/alerts-19.html.
YAHOO, Inc. http://help.yahoo.com/help/us/alerts/alerts-09.html.
YAHOO, Inc. http://help.yahoo.com/help/us/alerts/alerts-06.html.
YAHOO, Inc. http://help.yahoo.com/help/us/alerts/alerts-13.html.
YAHOO, Inc. http://help.yahoo.com/help/us/alerts/alerts-23.html.
YAHOO, Inc. http://help.yahoo.com/help/us/alerts/alerts-10.html.
YAHOO, Inc. http://help.yahoo.com/help/us/alerts/alerts-24.html.
YAHOO, Inc. http://help.yahoo.com/help/us/mobile/alerts/alerts-09.html.
YAHOO, Inc. http://help.yahoo.com/help/us/alerts/alerts-25.html.
YAHOO, Inc. http://help.yahoo.com/help/us/alerts/alerts-26.html.
YAHOO, Inc. http://help.yahoo.com/help/us/alerts/alerts-22.html.
YAHOO, Inc. http://help.yahoo.com/help/us/tips.html.
YAHOO, Inc. http://help.yahoo.com/.
YAHOO, Inc. http://help.yahoo.com/help/us/alerts/alerts-07.html.
FitSense Technology, Inc., http://www.fitsense.com.
FitSense Technology, Inc., http://www.fitsense.com/SystemDevice.aspx.
FitSense Technology, Inc., http://www.fitsense.com/Network.aspx.
FitSense Technology, Inc., http://www.fitsense.com/Wireless.aspx.
FitSense Technology, Inc., http://www.fitsense.com/FS1.aspx.
FitSense Technology, Inc., http://www.fitsense.com/WeightManagement.aspx.
FitSense Technology, Inc., http://www.fitsense.com/HealthWellness.aspx.
FitSense Technology, Inc., http://www.fitsense.com/DiseaseManagement.aspx.

* cited by examiner

METHOD AND APPARATUS TO PROVIDE AN INTERFACE TO OBTAIN DATA FROM A REAL-TIME MONITOR

FIELD OF THE INVENTION

The present invention relates to monitors, and more particular to obtaining data from real-time monitors.

BACKGROUND

Various manufacturers are starting to introduce health monitors that are non-invasive. For example, the Glucoband by Calisto Medical is a compact electronic scanning device that utilizes a bio-electromagnetic resonance phenomenon to non-invasively measure blood glucose levels in the human body, and to continuously monitor the blood glucose level. These devices are designed to stay on the user's body, and periodically provide testing and test results. The wristwatch-like Glucoband, for example, includes a fully integrated LCD screen, and can provide continuous monitoring. The results of the testing and monitoring are output on the integrated LCD screen. Such monitoring devices are becoming more and more common, ranging from health monitors to environmental monitors, weather, traffic, and other monitors.

The prior art system is thus designed to provide real-time data to the patient. However, it may be advantageous to provide the ability for a doctor, or other professional, to monitor the trends and historical data from such devices.

SUMMARY OF THE INVENTION

A method and apparatus to provide a server to collect data from continuously-used monitors is described, the server capable of storing historical data and making historical data, and data analysis available.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described is designed to be integrated with, or used in conjunction with, continuous monitors. These continuous monitors may be health monitors, such as the wristwatch glucose monitor, environmental monitors, such as monitors that measure salination levels in rivers, or other monitors that provide continuous, or pseudo-continuous data. In general, these devices were designed to provide real-time data on a local output, such as an integrated LCD screen. The present invention is focused on providing a way to save this real-time data, and enable review of historical data, and data trends at a later time.

Figure 1A:
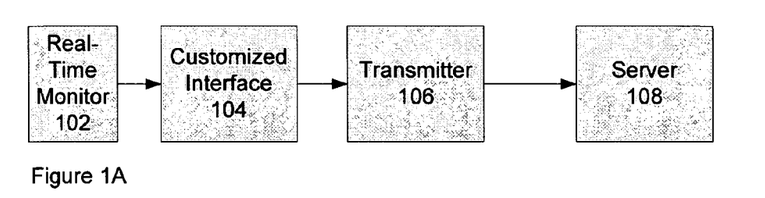
FIGS. 1A-F are block diagrams of various embodiments of the monitor and sending logic.

FIG. 1A is a block diagram of one embodiment of the monitor and sending logic. Note that while the term "real-time monitor" is used, the term applies to any sensor, monitor, device (SMD) which is periodically updated with actual data derived from its environment. For example, a real-time monitor may be a health monitor (such as a heart monitor or glucose monitor), an environmental monitor (such as a wind or rain monitor), state, or other type of monitor, sensor, or device.

The actual form factor, manufacturer, and output mechanism of the real-time monitor 102 is irrelevant to the functioning of the present invention. However, the customized interface 104 is designed to be fitted for the particular monitor 102. In one embodiment, the customized interface 104 may use the output mechanism of the real-time monitor 102. Alternatively, the customized interface 104 may be more closely related to the real-time monitor 104. The customized interface 104 obtains the data from the real-time monitor 102. The transmitter 106, which may include a receiver as well in one embodiment, then sends the data from the real-time monitor 102 to a remote server 108. The remote server 108, in one embodiment, integrates the data from the real-time monitor 102 to create a virtual monitor which includes the pseudo-real-time data just received, as well as historical data.

In one embodiment, data is sent to the remote server using WiFi (wireless fidelity), SMS (short message service), MMS (multimedia message service), Network protocols like email (electronic mail) and IM (instant messaging), MAN (metropolitan area network), LAN (local area network), cellular protocols (such as CMDA or GMS), or another system.

Figure 1B:
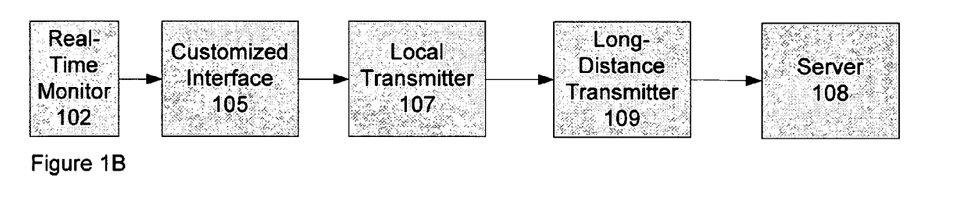

In one embodiment, shown in FIG. 1B, the transmission of the data is a two-stage process, first via a local transmitter, and then via a long-distance transmitter. In one embodiment, for local transmission, from the interface to the long-distance transmitter, Bluetooth, RFID (radio frequency identification), WiFi, personal area network, or an alternative system may be used.

In one embodiment, local transmitter 105 may be a built-in part of the SMD 101. For example, in one embodiment, an SMD may include a Bluetooth transmitter. The long-distance transmitter may then pick up the Bluetooth transmission, and send it to the remote server.

In one embodiment, the long-distance transmitter is a cellular telephone handset. The handset may be Bluetooth enabled, and receive data from the real-time sensor, which may have a Bluetooth transmitter built in, or may have a local transmitter attached to it through another means. The handset may operate as the long-distance transmitter using a software application which receives the data from the real-time monitor, packages it in an appropriate format, such as SMS or MMS, and sends it via its normal cellular protocol (CMDA/GMS/etc.) to the server.

FIGS. 1C through 1F illustrate various types of interfaces, while FIGS. 2A through 5 illustrate implementations of the various interfaces.

Figure 1C:
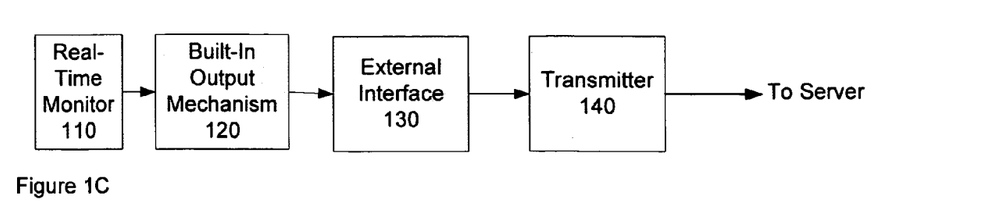
Figure 4A:
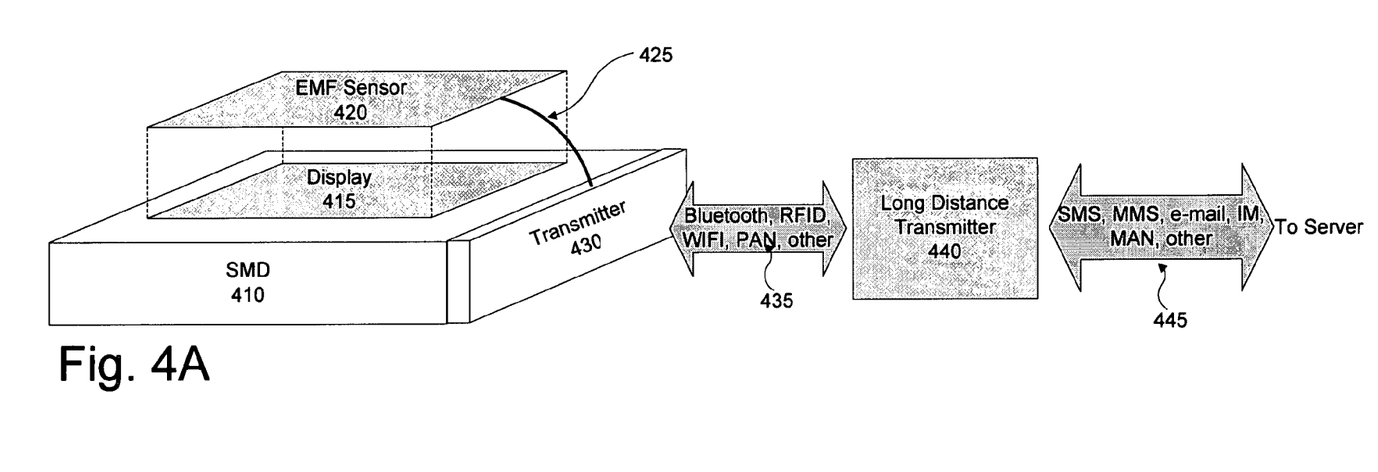
FIGS. 4A-B illustrate two exemplary external capture mechanisms.
Figure 4B:
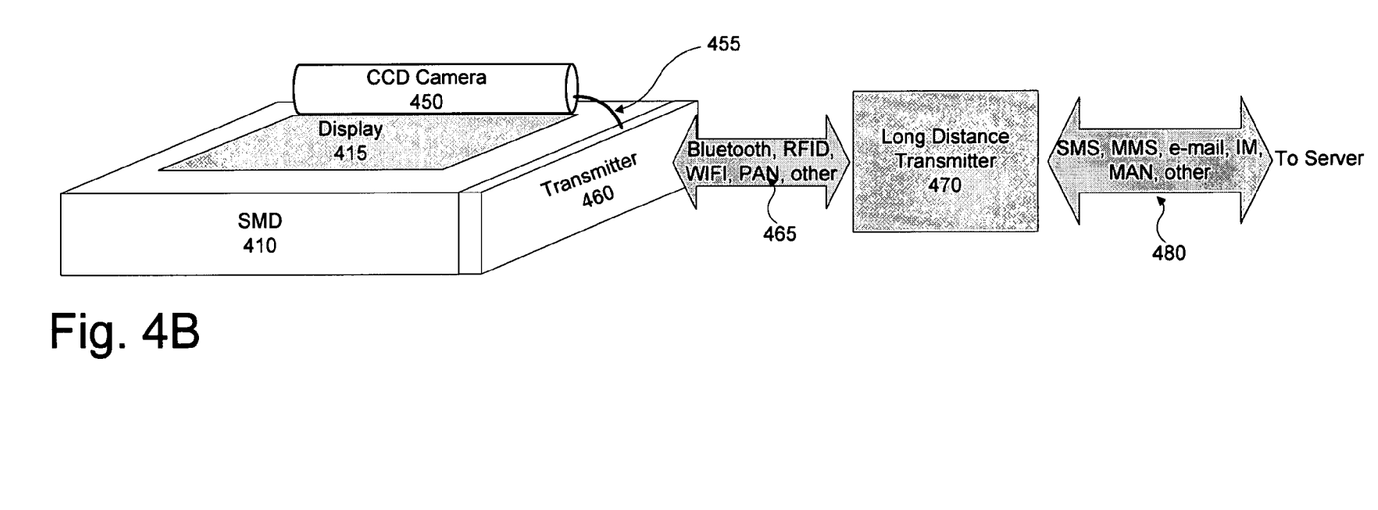

FIG. 1C illustrates an external interface 130, which is added in a way that uses the built-in output mechanism 120 of the underlying real-time monitor 110. For example, if the built-in output mechanism 120 is an LCD (liquid crystal display) or similar display, the external interface 130 may be a charge coupled device (CCD) 450 to capture the image, as shown in FIG. 4B. Alternatively, the external interface 130 may be an EMF (electro-magnetic force) sensor 420 which senses the data being written to the output mechanism 120, as shown in FIG. 4A. Alternatively, if the output is for example recording paper—such as for some heart monitors—the system may read the recording using a camera, line scanner, or similar device.

Figure 1D:
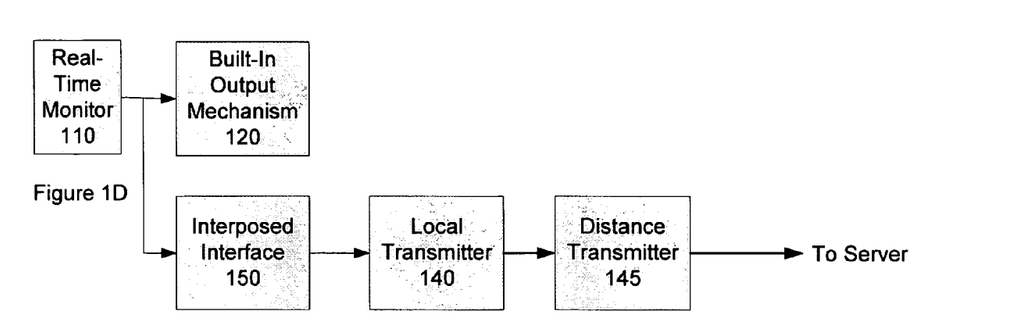

FIG. 1D illustrates one embodiment of an interposed interface 150. The interposed interface 150 works in parallel with the built-in output mechanism 120, and obtains its data through other means. Exemplary interposed interfaces include having the interface access the data through an existing data output, or another means of obtaining the data from the sensor itself, without going through the built-in output mechanism, or integrating circuits within the SMD itself. Touching the internal circuitry of the SMD may require an additional FDA approval cycle. Thus, interposed interface 150, in one embodiment, is placed so as to not require such an approval.

Figure 2A:
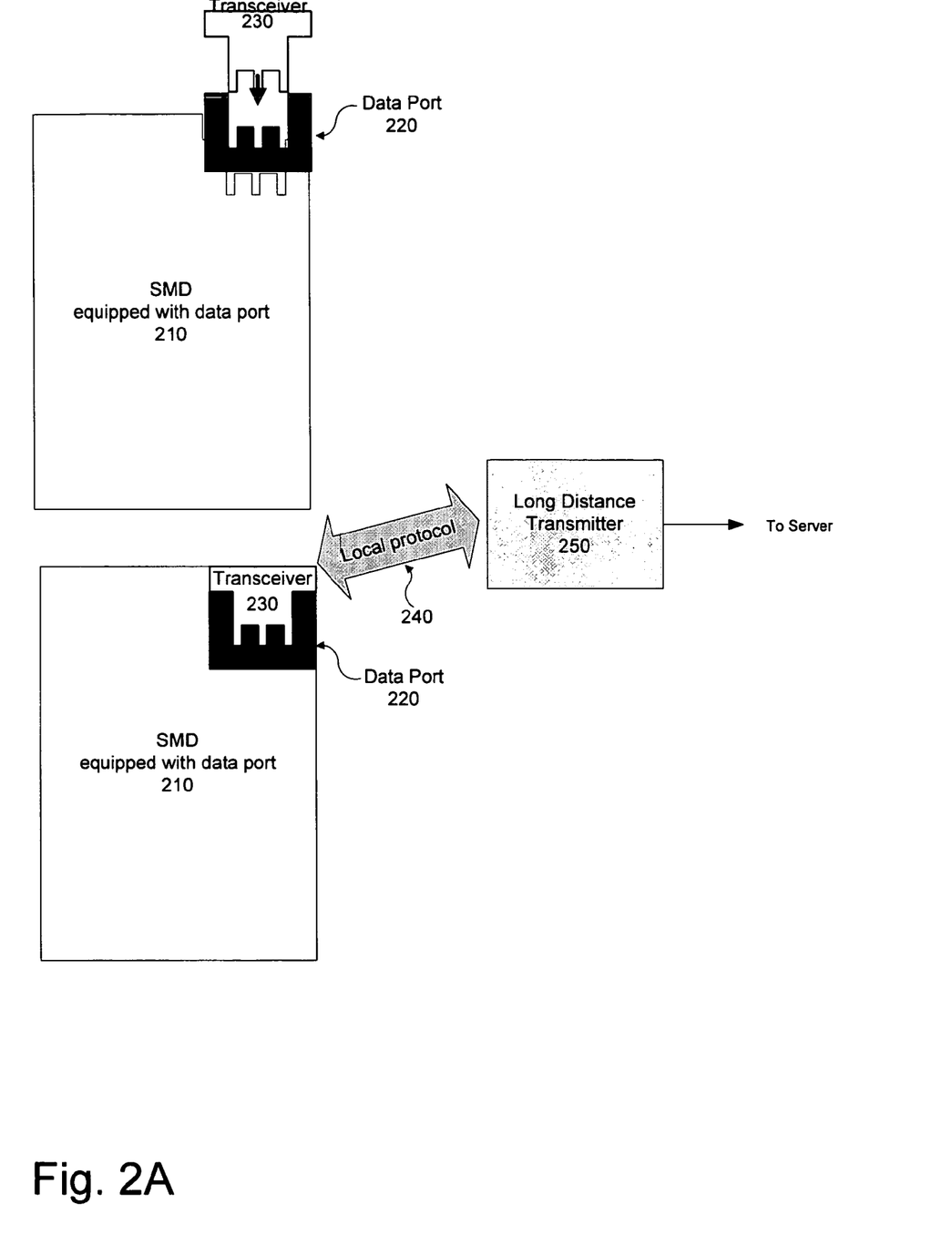
FIGS. 2A-B illustrate one exemplary external capture mechanism.
Figure 2B:
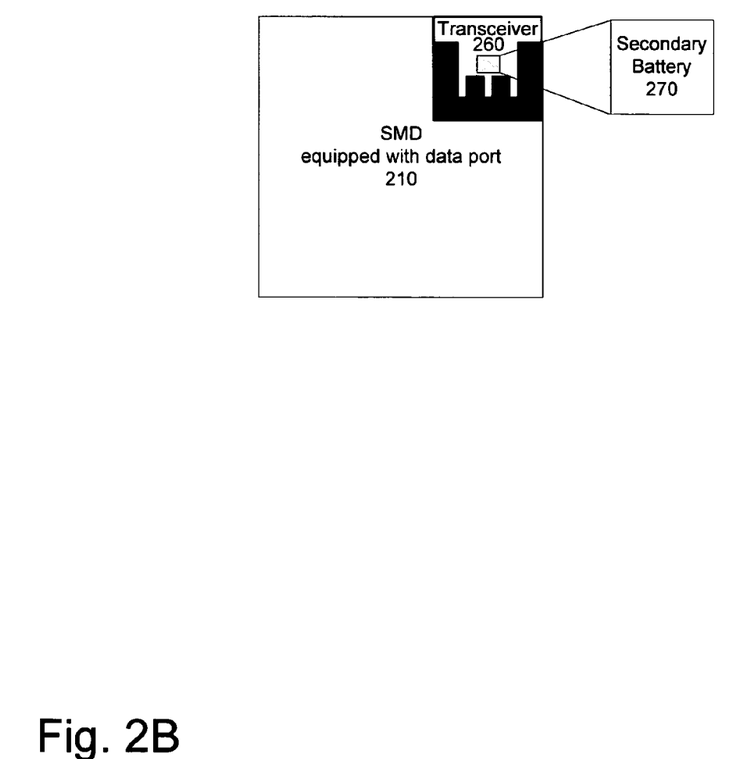

FIG. 2A illustrates an exemplary interposed interface 130 in transceiver 230. Transceiver 230, which in the alternative may be simply a transmitter without receiving capability, is designed to fit into the data port 220 of the real-time monitor 210. Some real-time monitors 210 come equipped with a data port 220. The transceiver 230, which is the external interface, receives the data formatted for output from the data port 220. In one embodiment, the transceiver 230 is sized to fit easily into the data port, and to permanently reside in the data port. In one embodiment, as shown in FIG. 2B, the transceiver 260 includes a battery 270. Alternatively, many transceivers are powered by the device, and the transceiver 230 may draw power from its host SMD.

As shown in FIG. 2A, the interposed interface may transmit locally, and be retransmitted by another device. For example, the interposed interface may transmit data in Bluetooth format. This data may be received by a cellular telephone, which may then in turn retransmit the data to a server. In one embodiment, the transceiver itself may include a cell phone circuit, enabling it to directly transmit from the transceiver to the server.

Figure 1E:
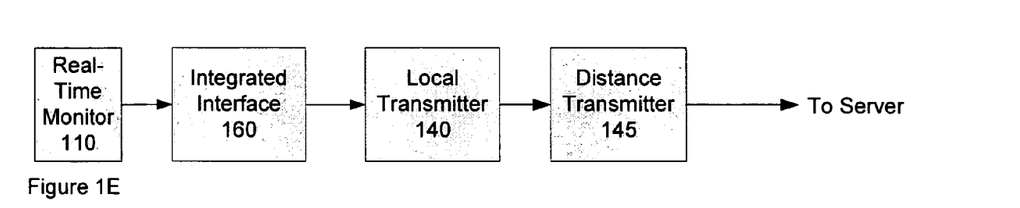
Figure 1F:
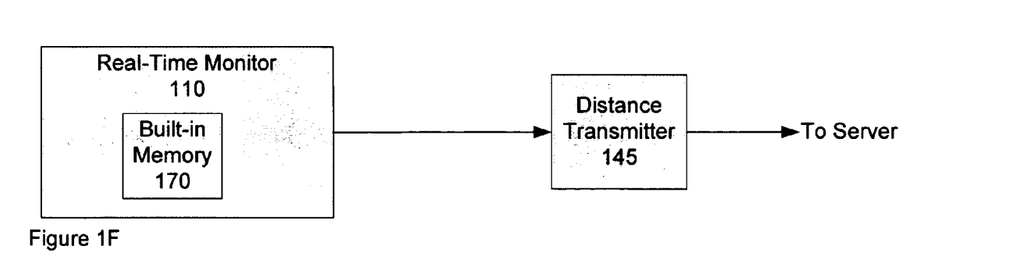
Figure 5:
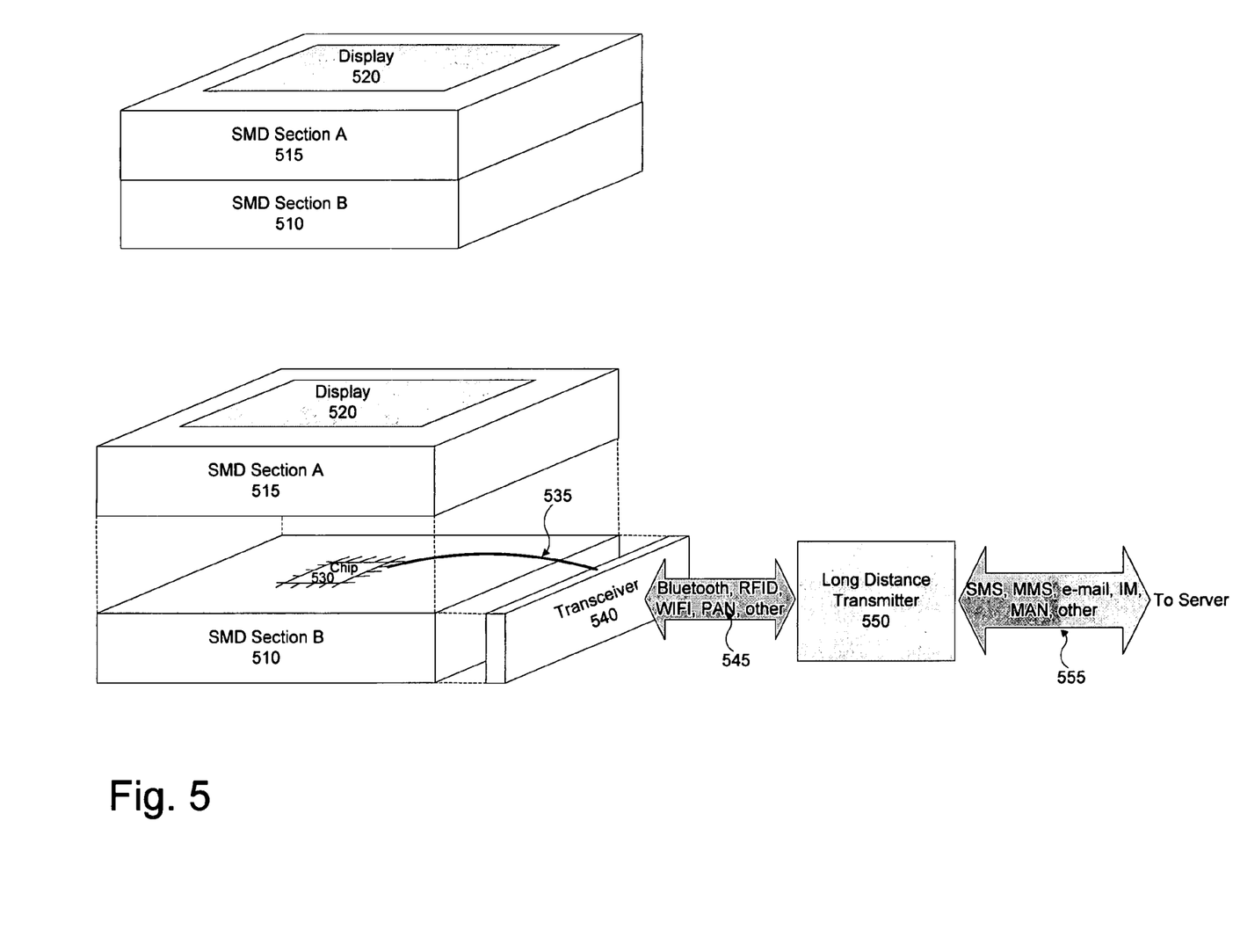
FIG. 5 illustrates an exemplary integrated capture mechanism.

FIG. 1E illustrates one embodiment of an integrated interface. An integrated interface is inserted within the real-time monitor 110 itself. In one embodiment, the integrated transceiver may receive its data directly from the SMD's chip, as shown in FIG. 5. In one embodiment, integrating the integrated transceiver into the SMD may require adding a direct connection to internal circuitry within the SMD. The integrated transceiver, in one embodiment, may reside within the SMD 310/350. Alternatively, the integrated SMD may simply include an internal connection to the SMD, with the transceiver itself residing outside the SMD. Both alternatives are shown in FIG. 5.

Figure 3A:
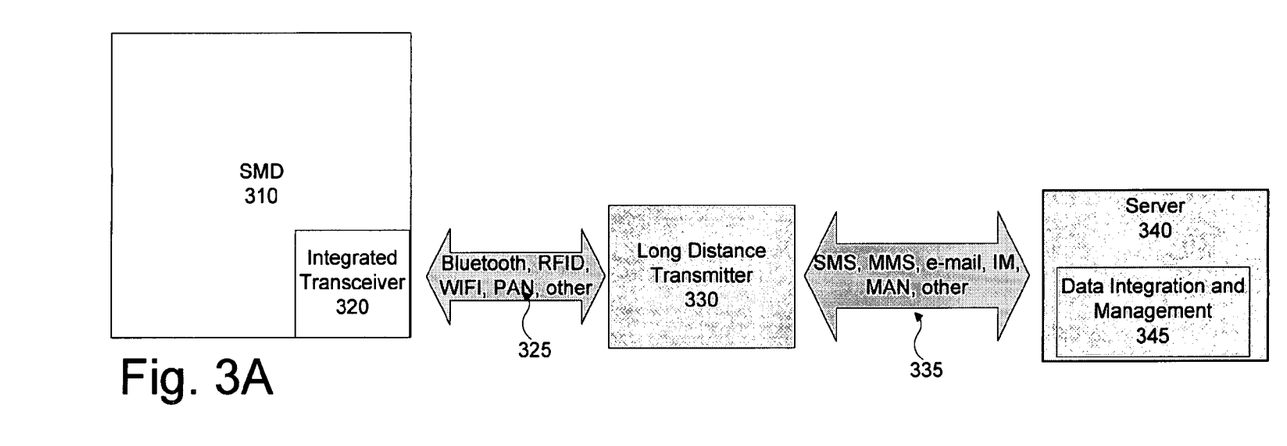
FIGS. 3A-B illustrate exemplary internal capture mechanisms.
Figure 3B:
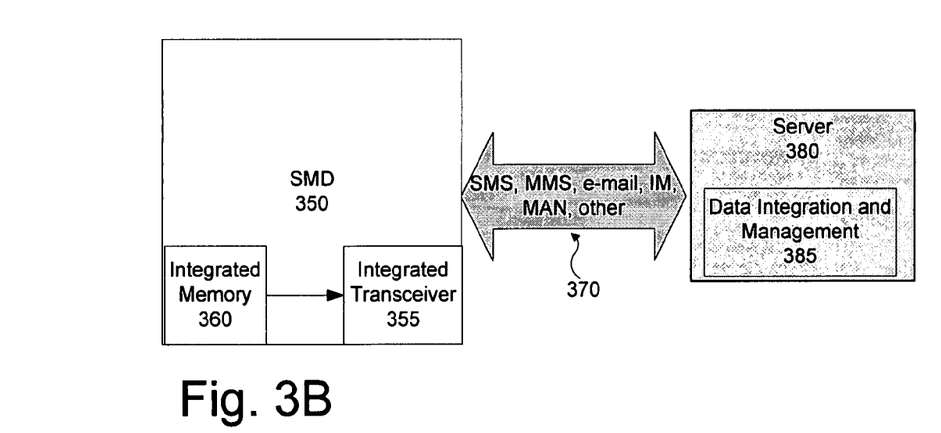

FIGS. 3A and 3B illustrate exemplary embodiments of using an integrated transceiver 320, 355. In one embodiment, the integrated transceiver 355 may use the built-in memory 360 of the SMD 350, and transmit stored data. This enables the transceiver 355 to transmit periodically, with a period that does not match the period of the SMD data. Alternatively, the transceiver 355 may include a separate memory.

In one embodiment, the communication between the SMD and the server is one-way, if the interface is a transmitter, and cannot receive data. This means that there is no way for the server to query the transmitter or indicate that a data set was not received. In one embodiment, the transmitter may transmit, in addition to the current data set, some historical data as well. This ensures that even if there is packet loss, all of the data is received.

Figure 6:
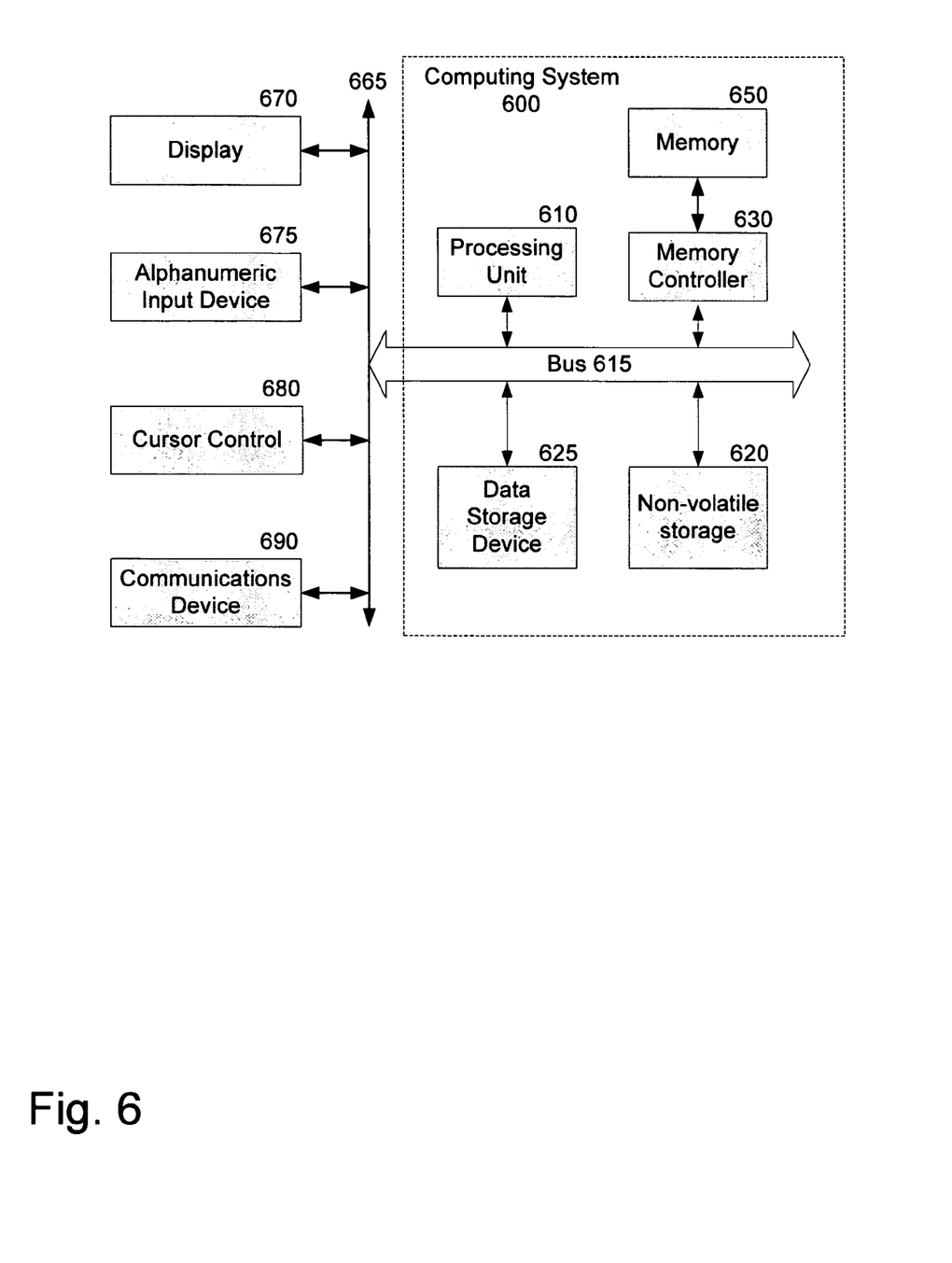
FIG. 6 is a block diagram of one embodiment of a computer system which may be used with the present invention.

FIG. 6 is one embodiment of a computer system that may be used with the present invention. It will be apparent to those of ordinary skill in the art, however that other alternative systems of various system architectures may also be used.

The data processing system illustrated in FIG. 6 includes a bus or other internal communication means 615 for communicating information, and a processor 610 coupled to the bus 615 for processing information. The system further comprises a random access memory (RAM) or other volatile storage device 650 (referred to as memory), coupled to bus 615 for storing information and instructions to be executed by processor 610. Main memory 650 also may be used for storing temporary variables or other intermediate information during execution of instructions by processor 610. The system also comprises a read only memory (ROM) and/or static storage device 620 coupled to bus 615 for storing static information and instructions for processor 610, and a data storage device 625 such as a magnetic disk or optical disk and its corresponding disk drive. Data storage device 625 is coupled to bus 615 for storing information and instructions.

The system may further be coupled to a display device 670, such as a cathode ray tube (CRT) or a liquid crystal display (LCD) coupled to bus 615 through bus 665 for displaying information to a computer user. An alphanumeric input device 675, including alphanumeric and other keys, may also be coupled to bus 615 through bus 665 for communicating information and command selections to processor 610. An additional user input device is cursor control device 680, such as a mouse, a trackball, stylus, or cursor direction keys coupled to bus 615 through bus 665 for communicating direction information and command selections to processor 610, and for controlling cursor movement on display device 670.

Another device, which may optionally be coupled to computer system 600, is a communication device 690 for accessing other nodes of a distributed system via a network. The communication device 690 may include any of a number of commercially available networking peripheral devices such as those used for coupling to an Ethernet, token ring, Internet, or wide area network. The communication device 690 may further be a null-modem connection, a wireless connection mechanism, or any other mechanism that provides connectivity between the computer system 600 and the outside world. Note that any or all of the components of this system illustrated in FIG. 6 and associated hardware may be used in various embodiments of the present invention.

It will be appreciated by those of ordinary skill in the art that any configuration of the system may be used for various purposes according to the particular implementation. The control logic or software implementing the present invention can be stored in main memory 650, mass storage device 625, or other storage medium locally or remotely accessible to processor 610.

It will be apparent to those of ordinary skill in the art that the system, method, and process described herein can be implemented as software stored in main memory 650 or read only memory 620 and executed by processor 610. This control logic or software may also be resident on an article of manufacture comprising a computer readable medium having computer readable program code embodied therein and being readable by the mass storage device 625 and for causing the processor 610 to operate in accordance with the methods and teachings herein.

The present invention may also be embodied in a handheld or portable device containing a subset of the computer hardware components described above. For example, the handheld device may be configured to contain only the bus 615, the processor 610, and memory 650 and/or 625. The present invention may also be embodied in a special purpose appliance including a subset of the computer hardware components described above. For example, the appliance may include a processor 610, a data storage device 625, a bus 615, and memory 650, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 610. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

In the foregoing specification, the invention has been described with reference to specific exemplary embodiments thereof. In particular, various formats were described in the alternative. One of skill in the art understands that the features described with respect to the various embodiments can be mixed and matched together to form a system. Furthermore, it will be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An add-on transmission system to a sensor, monitor, or device (SMD), the add-on transmission system to transparently capture the output of the SMD that cannot directly communicate with a server, the add-on transmission system further to transmit the output of the SMD to the server without requiring user action, the transmission system comprising:
    an interface to automatically receive data from the SMD;
    a transmitter to wirelessly transmit the data received by the interface to the remote server.

2. The system of claim 1, wherein the interface is a charge coupled device (CCD), to capture an image from an SMD display.

3. The system of claim 1, wherein the interface is an electromagnetic field detector, to detect the emissions from an SMD display.

4. A plug-in apparatus to provide server-transmission from a sensor, monitor, or device (SMD) that can not directly address a remote server, the plug-in apparatus comprising:
    an interface to automatically receive data from the SMD without requiring user interaction, and without interfering with or affecting SMD functionality; and
    a transmitter to wirelessly transmit the data from the SMD to the remote server, the data from the SMD representing monitoring results.

5. The plug-in apparatus of claim 4, wherein the interface is a data port designed to receive a wired connection.

6. The plug-in apparatus of claim 4, wherein the interface is a charge coupled device (CCD), to capture an image from an SMD display.

7. The plug-in apparatus of claim 4, wherein the interface is an electromagnetic field detector, to detect the emissions from an SMD display.

8. The plug-in apparatus of claim 4, wherein the interface is a wire connection to a graphics circuit within the SMD, to receive output from the graphics circuit within the SMD.

* * * * *